(12) United States Patent
Schoenfeld et al.

(10) Patent No.: US 6,533,756 B2
(45) Date of Patent: Mar. 18, 2003

(54) SINGLE USE SYRINGE

(75) Inventors: Joel Schoenfeld, Woodbury; Randy Cohen, Melville, both of NY (US)

(73) Assignee: Univec, Inc., Farmingdale, NY (US)

( * ) Notice: Subject to any disclaimer, the term of this patent is extended or adjusted under 35 U.S.C. 154(b) by 6 days.

(21) Appl. No.: 09/781,747

(22) Filed: Feb. 12, 2001

(65) Prior Publication Data

US 2001/0049506 A1 Dec. 6, 2001

Related U.S. Application Data

(60) Provisional application No. 60/181,592, filed on Feb. 10, 2000.

(51) Int. Cl.[7] ............................................. A61M 5/00
(52) U.S. Cl. ..................... 604/110; 604/604; 604/220
(58) Field of Search .................................. 604/110, 220

(56) References Cited

U.S. PATENT DOCUMENTS 5,205,825 A * 4/1993 Allison et al. .............. 604/110
5,562,623 A * 10/1996 Shonfeld et al. ............ 604/110

* cited by examiner

Primary Examiner—Philippe Derakshani
(74) Attorney, Agent, or Firm—Levisohn, Lerner, Berger & Langsam, LLP

(57) ABSTRACT

A single-use syringe having a barrel and a plunger is provided. The plunger at least one vane, and the vane is provided with serrations or ratchet teeth. The serrations each have a vertical rear wall and a sloped top edge. A barbed clip is provided that fits on the serrated vane. The barbs on the clip engage the inner wall of the barrel. When the plunger is initially withdrawn, the barbs of the clip engage the inner wall of the barrel and the clip remains in position with respect to the barrel. Because the tops of the serrations are sloped, the ridged/serrated vane of the plunger passes easily under the clip. When the plunger is re-inserted into the barrel, the clip engages one of the vertical rear walls of the serrations and moves along with the plunger deeper into the barrel. If one attempts to re-retract the plunger, the distal wall of the plunger strikes the clip, and the clip is immobilized because the barbs engage the inner wall of the barrel.

20 Claims, 2 Drawing Sheets

SINGLE USE SYRINGE

This application claims the benefit of provisional application No. 60/181,592 filed Feb. 10, 2000.

BACKGROUND OF THE INVENTION

1. Field of the Invention

The invention relates to disposable syringes; more particularly, the invention relates to disposable syringes which may be used only once and inherently prevent a second use from occurring.

2. Description of the Related Art

Plastic hypodermic syringes are mass-producible, and are intended to be sterilized or discarded after only one use to prevent the spread of blood-borne diseases such as hepatitis and AIDS from one user to the next. For example, if an individual using a syringe is carrying a blood-borne disease, a subsequent user of the syringe runs a great risk of contracting the disease.

Plastic hypodermic syringes which are not pre-filled with medication are usually loaded by the action of a plunger which creates a reduced pressure in the barrel and results in the intake of fluid into the barrel. Such syringes depend on a rubber seal attached to the plunger to ensure that a reduced pressure can be effected because of the wider tolerances experienced in plastic molding, in contrast to precisely ground glass syringes which do not require a rubber seal.

One example of a syringe that can be used only one time is described in U.S. Pat. No. 5,205,825 to Allison et al., the teachings of which are incorporated by reference herein. The device described by Allison et al. includes a conventional plastic plunger (which is X-shaped in section) and a plastic barrel. A metal clip is positionable between the plunger and the inner wall of the barrel. The clip includes two pairs of barbs. One pair of outer barbs is intended to engage the inner wall of the barrel and the other pair of barbs is intended to engage the vane walls of the plunger. The barbs are angled to allow the plunger to be withdrawn from the barrel for medication loading. The clip stays motionless relative to the barrel when the plunger is withdrawn, because the outer barbs dig into the inner wall of the barrel. When the plunger is pushed back into the barrel to expel the liquid inside, the inner barbs of the clip engage the plunger, and the clip moves with the plunger with respect to the barrel. If one attempts to withdraw the plunger a second time, the clip and plunger remain in place because the outer barbs of the clip again dig into and engage the inner barrel wall, and the distal end of the plunger strikes the immobile clip.

The Allison et al. device suffers from several drawbacks. First, the clip described is difficult to manufacture. Second, proper placement of the clip with respect to the plunger is difficult to gauge by eye. In other words, it is difficult to pre-measure the proper dosage (for a pre-filled syringe) or draw the correct amount of medication into an empty syringe utilizing the Allison et al. clip. Third, during manufacture and assembly of the syringe, it is difficult to ensure that the clip is properly positioned relative to the plunger and barrel because the clip can slip backwardly during placement.

SUMMARY OF THE INVENTION

Accordingly, it is an object of the invention to provide a disposable hypodermic syringe which cannot be used more than once.

It is another object of the invention to provide a disposable hypodermic syringe which immobilizes the plunger inside the barrel after a single use.

It is another object of the invention to provide a disposable hypodermic syringe which is easy and inexpensive to manufacture and assemble.

The above and other objects are achieved by the invention which is a hypodermic syringe. The syringe has a barrel and a plunger. The plunger has a distal wall and at least one vane, and the vane is provided with serrations or ratchet teeth. The serrations each have a vertical rear wall and a sloped top edge, the slope angling downward in a forward (distal) direction. A barbed clip is provided that fits on the serrated vane. The barbs on the clip engage the inner wall of the barrel.

When the plunger is withdrawn for drawing medication into the barrel, the barbs of the clip dig into and engage the inner wall of the barrel and the clip remains in position with respect to the barrel. For pre-filled syringes, the plunger does not need to be withdrawn. Because the tops of the serrations are sloped, the ridged/serrated vane of the plunger passes easily under the stationary clip. When the plunger is re-inserted into the barrel, the clip engages one of the vertical rear walls of the serrations and moves along with the plunger deeper into the barrel (distally). If one attempts to re-retract the plunger, the distal wall of the plunger strikes and abuts the clip, and the clip is immobilized because the barbs engage and dig into the inner wall of the barrel.

It is easy to position the clip precisely on the plunger during manufacture of the invention owing to the serrations on one or more of the vanes. Once the clip is positioned, it cannot slip backwardly with respect to the plunger because a) the barbs engage the barrel, and b) the rear vertical walls of the serrations engage the rear portion of the clip and prevent backslip. Further, it is much easier to meter doses of the contents of a syringe because of the prevention of the backslip of the clip and because dose indicators can be printed or formed on the serrations, for example. The inventive clip is also easy to manufacture.

DETAILED DESCRIPTION OF THE PREFERRED EMBODIMENTS AND THE DRAWINGS

Figure 1:
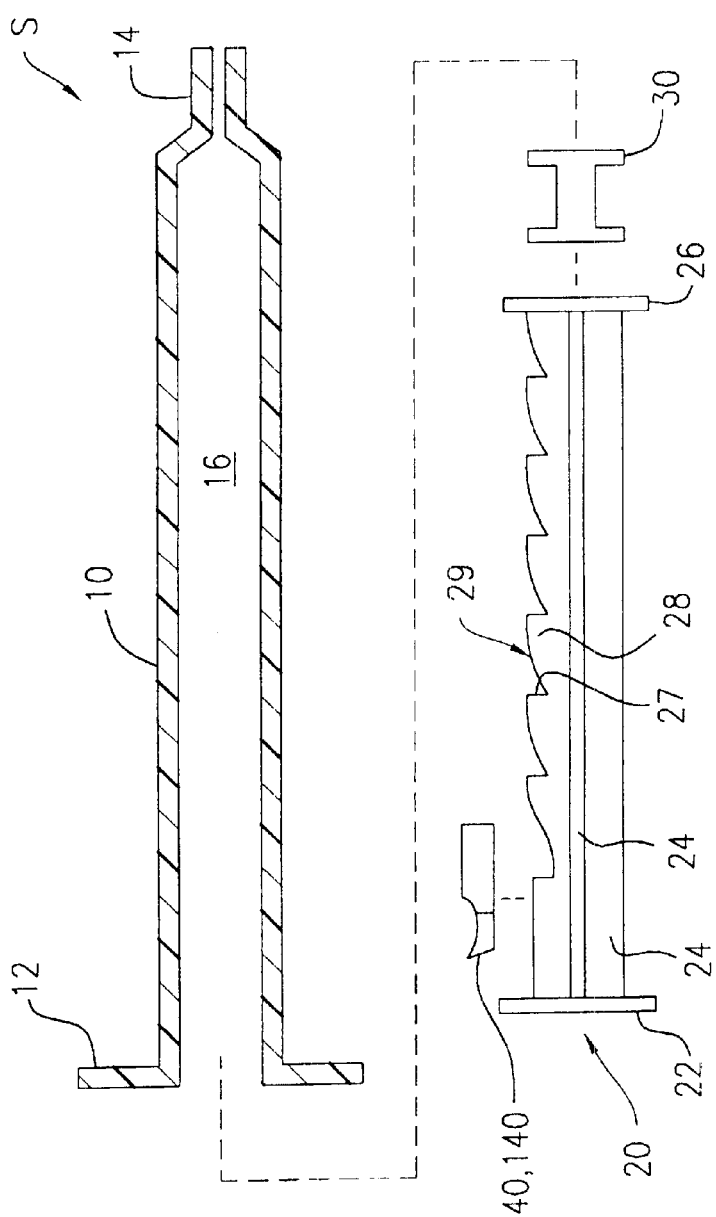
FIG. 1 is an exploded partial section view of a disposable syringe according to the invention.
Figure 2:
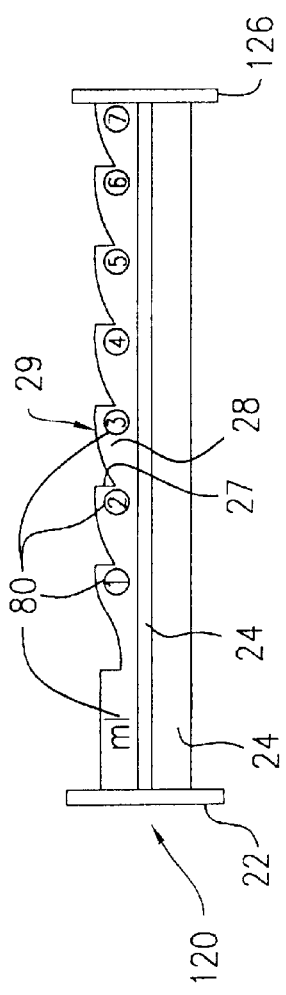
FIG. 2 is a side view of an alternative plunger that may be used with the syringe of FIG. 1.

Description of the invention will now be given with reference to FIGS. 1–7. The inventive syringe 5 includes a barrel 10 having a proximal finger grip flange 12 and a distal needle holder 14. Insertable within the inner chamber 16 of barrel 10 is plunger 20. The syringe and plunger are preferably made of medical grade plastic, as is now conventional in disposable syringes. Plunger 20 includes a proximal thumb flange 22 and a distal disc 26. The central portion of the plunger is typically X-shaped in cross section and contains a plurality of vanes 24. One of the vanes is preferably provided with serrations or ratchet teeth 28. Each serration includes a rear wall 27, which is substantially perpendicular to the longitudinal axis of the plunger, and a sloped upper surface 29. As shown in FIG. 2, the serrations 28 may be provided with dosage indicia 80. For example, each serration 28 may represent 1 ml of medication. This provides the user a much easier way of determining a dose for dispensing. Instead of having to squint at small indicators marked all along the barrel, each macroscopic serration 28 can represent a specific unit of volume. The indicia 80 also assist the manufacturer of pre-filled syringes in properly placing clip 40 during assembly of the syringe.

A rubber stopper 30 may be provided attached to the distal end of the plunger, as in conventional syringes. Alternatively, as shown in FIG. 2, plunger 120 may be used in place of plunger 20. Distal disc 126 of plunger 120 is more rigid (i.e., has a higher durometer) than the rest of plunger 120 (which is preferably made of plastic) and can function in place of rubber stopper 30 by flexing the walls of barrel 10 outward as it passes through the barrel. Preferably, the diameter of disc 126 is dimensioned slightly larger than the diameter of inner chamber 16 so as to provide a liquid-tight seal.

Figure 3:
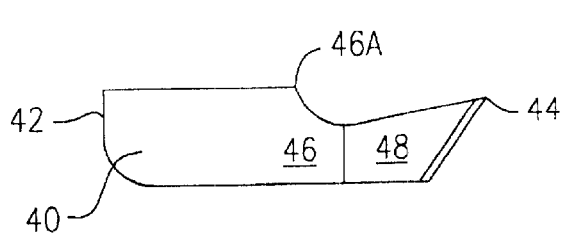
FIG. 3 is a side view of one embodiment of the inventive clip.
Figure 4:
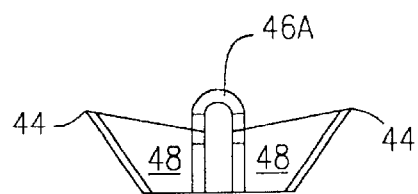
FIG. 4 is a front view of the inventive clip of FIG. 3.

Clip 40 is provided on the vane 24 of plunger 20 that has serrations 28. As shown in detail in FIGS. 3–6, clip 40 includes a blunt leading end 42 and a pointed trailing end 44. Towards the front portion of clip 40 is a U-shaped main body 46. Towards the rear portion of clip 40 are two rearwardly and outwardly projecting wings 48 which terminate in points 44. Wings 48 may be angled upwards as shown in FIG. 3, or they may be angled downwards as shown as wings 148 in FIG. 6.

Figure 5:
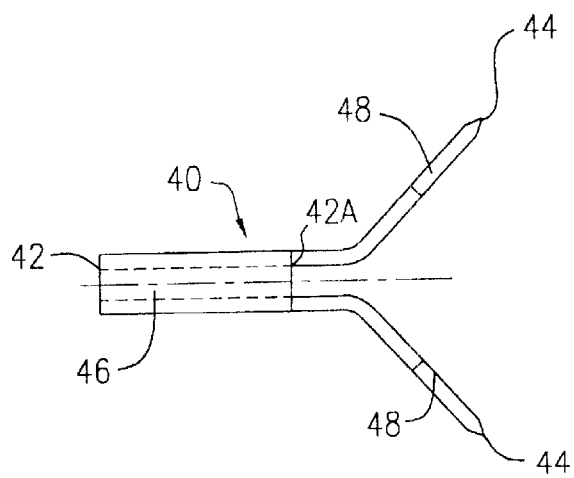
FIG. 5 is a top view of the inventive clip of FIGS. 3 and 4.
Figure 6:
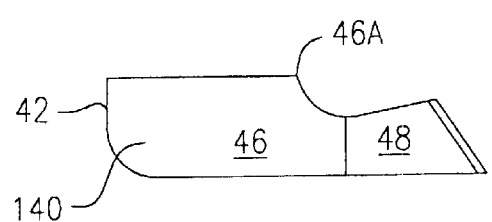
FIG. 6 is a side view of another embodiment of the inventive clip.

The U-shaped main body 46 (see FIG. 4) of clip 40 is designed to slide over the sloped surfaces 29 of serrations 28 when plunger 20 is initially withdrawn from barrel 10. Preferably, as shown in FIGS. 1 and 2, sloped surfaces 29 are curved to allow for a smoother ride of clip 40 over serrations 28. As plunger 20 is being withdrawn, the points 44 of wings 48 (or 148) engage the inner wall of barrel 10 and prevent the clip from moving backwardly with plunger 20. That is, the points 44 of wings 48 dig into the inner wall of barrel 10 and immobilize clip 40 when plunger 20 is being withdrawn to fill chamber 16. Once chamber 16 is filled with fluid, plunger 20 is forced forwardly into barrel 10. Then, rear surface 46A of main body 46 engages the first (i.e., the closest) of the rear vertical walls 27 of serrations 28. As a result, clip 40 is pushed along with plunger 20 as the plunger is re-inserted into the barrel. Points 44 of wings 48 contact the inner surface of barrel 10 but do not prevent the clip from moving deeper inside barrel 10 because wings 48 are angled rearwardly as shown in FIG. 5. The plunger is able to be pushed into barrel 10 to expel the entire contents of chamber 16. If a person attempts to withdraw the plunger for a second use of the syringe, distal disc 26 (or 126) will strike and abut blunt leading end 42 of clip 40 at the distal end of barrel 10 (i.e., close to needle holder 14). Points 44 of wings 48 engage and dig into the inner surface of barrel 10, and clip 40 is prevented from moving backwards along the barrel. Clip 40 thus prevents plunger 20 from being withdrawn from barrel 10 a second time and thus prevents syringe 5 from being used more than once. If the clip is sitting on top of a sloped surface 29 when it is finally immobilized at the distal end of barrel 10, the slope of the surface 29 angles the front end of the clip upwards, and the rear surface 46A of U-shaped main body 46 is preferably forced against the inner wall of barrel 10. In this way, clip 40 provides up to three points of contact with barrel 10 to ensure that it will not be pushed backwards by a person attempting to withdraw the plunger a second time.

Figure 7:
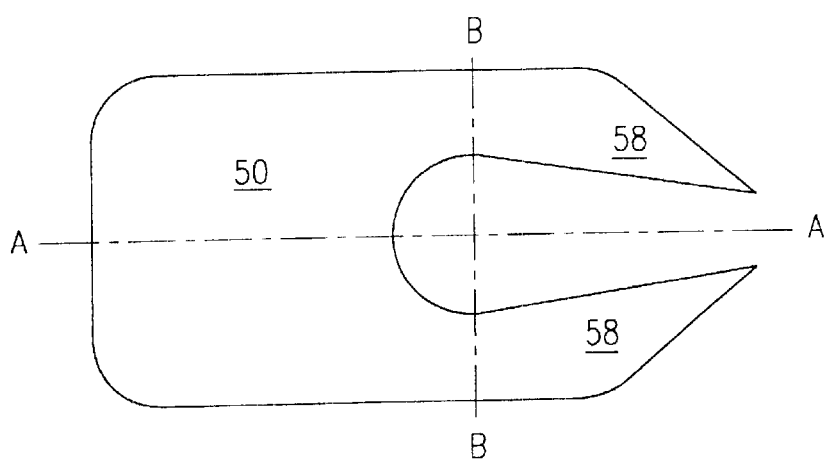
FIG. 7 is a top elevational view of a sheet metal blank that is used to manufacture the inventive clip prior to the blank being folded into the proper configuration.

FIG. 7 depicts a sheet metal blank 50, preferably stainless steel, from which the inventive clip is made. In one step, blank 50 is folded about line A to produce the U-shaped body 46. Line A corresponds roughly to the longitudinal axis of blank 50. In another step, each wing 48 is created by folding each prong 58 approximately 45 degrees along lines B away from line A.

The invention is not limited to the above description or to what is shown in the attached Figures, which are illustrative in nature only. For example, plungers 20, 120 are shown with one vane having serrations 28. However, serrations may be provided on two or more vanes of the plunger. Having serrations on more than one vane facilitates the assembly of the syringe, because the clip need not be aligned with only one possible vane of the plunger; i.e., if in the manufacturing process, the clip falls on any of the serrated vanes, the clip does not need to be repositioned. Different vanes can be provided with differently-spaced serrations to allow for much greater variation in types dosages to be metered out. For example, one vane may be provided with milliliter serrations, while another vane may be provided with half-milliliter serrations. Also, the plungers are described and depicted as being X-shaped in cross-section, i.e., having four vanes. However, any number of vanes as is practical may be provided on the plungers. The plunger may also be provided with a weakened portion at or near its distal end. Thus, if a person attempts to withdraw the plunger a second time, the plunger will break at its weakened portion, leaving the distal end attached to the rubber stopper (or the disc) and rendering the syringe unusable.

What is claimed is:

1. A single-use syringe comprising:
    a barrel, having an interior volume, an inner wall, and a distal end;
    a plunger disposable inside said interior volume of said barrel, said plunger having a distal wall and at least one longitudinal vane, said at least one vane having at least one serration; and
    a barbed clip having at least one point, said point engageable with said inner wall of the barrel, said barbed clip fittable on said vane having said at least one serration,
    wherein when said plunger is initially withdrawn from said barrel, said at least one point engages said inner wall of said barrel to prevent movement of said barbed clip relative to said barrel and said at least one vane slides under said barbed clip, and wherein when said plunger is then inserted into said barrel, said barbed clip catches on said at least one serration and moves distally along with said plunger.

2. A single use syringe according to claim 1, wherein when said plunger has been inserted into said barrel and is attempted to be withdrawn out of said plunger, said at least one point lockingly engages said inner wall of said barrel and said distal wall abuts said barbed clip, thereby preventing removal of said plunger from said barrel.

3. A single-use syringe according to claim 1, wherein said serration comprises a vertical rear wall and a sloped top edge, wherein when said plunger is initially withdrawn from said barrel, said sloped top edge of said serration slides under said barbed clip, and when said plunger is then inserted into said barrel, said barbed clip engages said vertical rear wall of said serration and moves distally along with said plunger.

4. A single-use syringe according to claim 1, wherein said at least one vane is provided with a plurality of serrations, each of said serrations having a vertical rear wall and a sloped top edge, wherein when said plunger is initially withdrawn from said barrel, said sloped top edges of said serrations slide under said barbed clip, and when said plunger is then inserted into said barrel, said barbed clip engages one of said vertical rear walls of one of said serrations.

5. A single use syringe according to claim 3, wherein when said plunger has been inserted into said barrel and is attempted to be withdrawn out of said plunger, said at least one point digs into and lockingly engages said inner wall of said barrel and said distal wall abuts said barbed clip, thereby preventing removal of said plunger from said barrel.

6. A single use syringe according to claim 4, wherein when said plunger has been inserted into said barrel and is attempted to be withdrawn out of said plunger, said at least one point lockingly engages said inner wall of said barrel and said distal wall abuts said barbed clip, thereby preventing removal of said plunger from said barrel.

7. A single-use syringe according to claim 1, said barbed clip comprising:

a blunt leading end having a rear surface; and a pointed trailing end, wherein when said plunger is inserted into said barrel, said rear surface of said blunt leading end engages said serration and said plunger pushes said barbed clip distally within said barrel.

8. A single-use syringe according to claim 7, wherein when said plunger is attempted to be withdrawn after having been inserted, said distal wall engages said blunt leading end and said pointed trailing end engages said inner wall of said barrel to thereby immobilize said plunger.

9. A single-use syringe according to claim 4, said barbed clip comprising:

a blunt leading end having a rear surface; and a pointed trailing end, wherein when said plunger is inserted into said barrel, said rear surface of said blunt leading end engages one of said vertical walls of one of said serrations.

10. A single-use syringe according to claim 9, wherein when said plunger is attempted to be withdrawn after having been inserted, said distal wall engages said blunt leading end and said pointed trailing end engages said inner wall of said barrel to thereby immobilize said plunger.

11. A single use syringe according to claim 7, said barbed clip further comprising:

a U-shaped main body which forms said blunt leading end having said rear surface; and at least one rearwardly projecting wing which terminates in a point which forms said pointed trailing end.

12. A single use syringe according to claim 11, wherein said rear surface of said U-shaped main body abuts said vertical rear wall when said plunger is inserted into said barrel, and wherein when said plunger is attempted to be withdrawn from said barrel, said distal wall abuts said U-shaped main body and said point on said rearwardly projecting wing digs into said inner wall of said barrel to thereby immobilize said plunger.

13. A single use syringe according to claim 9, said barbed clip further comprising:

a U-shaped main body which forms said blunt leading end having said rear surface; and at least one rearwardly projecting wing which terminates in a point which forms said pointed trailing end, wherein said rear surface of said U-shaped main body abuts one of said vertical rear walls when said plunger is inserted into said barrel, and wherein when said plunger is attempted to be withdrawn from said barrel said distal wall abuts said U-shaped main body and said point on said rearwardly projecting wing digs into said inner wall of said barrel to thereby immobilize said plunger.

14. A single use syringe according to claim 1, wherein said plunger is provided with a plurality of vanes, and wherein at least one serration is provided on more than one of said vanes.

15. A single use syringe according to claim 11, said barbed clip further comprising a plurality of rearwardly projecting wings each terminating respectively in a point.

16. A single use syringe according to claim 12, said barbed clip further comprising a plurality of rearwardly projecting wings each terminating respectively in a point, wherein said points on said rearwardly projecting wings dig into said inner wall of said barrel when said plunger is attempted to be withdrawn from said barrel.

17. A single use syringe according to claim 1, wherein said barbed clip is formed from a single flat sheet of material.

18. A single use syringe according to claim 11, wherein said barbed clip is formed from a single flat sheet of material having at least one prong adjacent a cutout, said U-shaped main body being formed by longitudinally bending said sheet and said at least one rearwardly projecting wing being formed by bending said prong away from said cutout.

19. A single use syringe according to claim 4, wherein a plurality of said serrations are each provided with indicia that indicate a dosage amount.

20. A single use syringe according to claim 14, wherein each of said plurality of vanes is provided with a plurality of said serrations, wherein one of said plurality of vanes is provided with first serrations spaced a first distance apart and a second of said plurality of vanes is provided with second serrations spaced a second distance apart, said second distance being different from said first distance.

* * * * *